United States Patent [19]

Jeffery et al.

[11] 4,443,449

[45] Apr. 17, 1984

[54] ARYLCYCLOBUTYLALKYLAMINES AND ANTI-DEPRESSION COMPOSITION AND METHODS USING SAME

[75] Inventors: James E. Jeffery; Eric C. Wilmshurst, both of Nottingham, England

[73] Assignee: The Boots Company Limited, Nottingham, England

[21] Appl. No.: 365,287

[22] Filed: Apr. 5, 1982

[30] Foreign Application Priority Data

Apr. 6, 1981 [GB] United Kingdom ............... 8110710

[51] Int. Cl.$^3$ ..................... A61K 31/135; C07C 87/28
[52] U.S. Cl. ..................................... 424/250; 424/263; 424/267; 424/274; 424/330; 544/403; 546/346; 546/348; 548/578; 564/428; 564/442; 564/305
[58] Field of Search ............... 564/305, 428, 442; 544/403; 546/346, 348; 548/578; 424/274, 267, 424/250, 263, 330

[56] References Cited

FOREIGN PATENT DOCUMENTS 973887 10/1964 United Kingdom.
1530172 10/1978 United Kingdom.

OTHER PUBLICATIONS

Arya et al., Ind. J. of Chem., vol. 14B, pp. 766–769, (1976).
Mndzhoyan et al., Armyanskii Khimichesdii Zhurnal, vol. 29, No. 2, pp. 194–199, (1976).

*Primary Examiner*—Henry R. Jiles
*Assistant Examiner*—Bernard Dentz
*Attorney, Agent, or Firm*—Gordon W. Hueschen

[57] ABSTRACT

Compounds of formula I

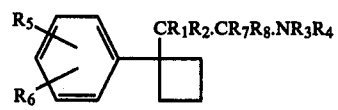

in which $R_1$ is H or $C_{1-3}$ alkyl; $R_2$ is H or $C_{1-3}$ alkyl; $R_3$ and/or $R_4$ are H, $C_{1-3}$ alkyl, $C_{3-6}$ alkenyl, $C_{3-6}$ alkynyl, $C_{3-7}$ cycloalkyl or $R_3$ and $R_4$ together with the nitrogen atom form a heterocyclic ring system; $R_5$ and/or $R_6$ are H, halo, $CF_3$, or $C_{1-3}$ alkyl (with the proviso that $R_5$ and $R_6$ cannot both be H or methyl) or $R_5$ and $R_6$ together with the carbon atoms to which they are attached form a second benzene ring and $R_7$ and/or $R_8$ are H or $C_{1-3}$ alkyl show therapeutic activity in the treatment of depression. Pharmaceutical compositions and processes for preparing compounds of formula I are disclosed.

32 Claims, No Drawings

ARYLCYCLOBUTYLALKYLAMINES AND ANTI-DEPRESSION COMPOSITION AND METHODS USING SAME

This invention relates to compounds having useful therapeutic activity particularly but not exclusively as antidepressants, to pharmaceutical compositions containing such compounds and to processes for the preparation of such compounds.

The present invention provides compounds of formula I

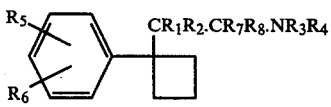

in which $R_1$ is H or an alkyl group containing 1 to 3 carbon atoms;

in which $R_2$ is H or an alkyl group containing 1 to 3 carbon atoms;

in which $R_3$ and $R_4$, which may be the same or different, are H, a straight or branched chain alkyl group containing 1 to 4 carbon atoms, an alkenyl group having 3 to 6 carbon atoms, an alkynyl group having 3 to 6 carbon atoms, or a cycloalkyl group in which the ring contains 3 to 7 carbon atoms, or $R_3$ and $R_4$ together with the nitrogen atom to which they are attached form an optionally substituted heterocyclic ring having 5 or 6 atoms in the ring which may contain further hetero atoms in addition to the nitrogen atom;

in which $R_5$ and $R_6$, which may be the same or different, are H, halo, trifluoromethyl, or an alkyl group containing 1 to 3 carbon atoms (with the proviso that $R_5$ and $R_6$ are not both H or methyl) or $R_5$ and $R_6$, together with the carbon atoms to which they are attached, form a second benzene ring; and in which $R_7$ and $R_8$ which may be the same or different are H or an alkyl group containing 1 to 3 carbon atoms and their pharmaceutically acceptable salts.

In the formulae included in this specification the symbol

represents a 1,1-disubstituted cyclobutane group of formula

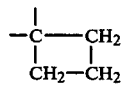

and $-CR_1R_2.CR_7R_8.NR_3R_4$ represents a group of formula

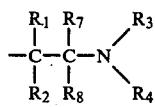

In the preferred compounds of formula I $R_1$ is H or methyl, and $R_2$ is H. In particularly preferred compounds of formula I both $R_1$ and $R_2$ are H.

In the preferred compounds of formula I, $R_3$ and/or $R_4$ are hydrogen, methyl, or ethyl or when $R_3$ and $R_4$ together with the nitrogen atom to which they are attached form a heterocyclic ring, the preferred compounds of formula I contain a heterocyclic group containing one nitrogen atom and 4 or 5 carbon atoms (e.g. pyrrolidinyl, piperidino) which is optionally substituted by one or more alkyl (e.g. methyl) groups (e.g. pyrrolidinyl substituted by two methyl groups), or form a heterocyclic group containing a second nitrogen atom which is optionally alkylated (e.g. 4-methylpiperazinyl) or form a heterocyclic group containing one or more double bonds (e.g. 1,2,3,6-tetrahydropyridyl).

In preferred compounds of formula I $R_5$ and/or $R_6$ which may be the same or different, are H, fluoro, chloro, bromo, iodo, trifluoromethyl, methyl, or $R_5$ and $R_6$ together with the carbon atom to which they are attached form a second benzene ring.

A first group of preferred compounds of formula I is represented by formula II

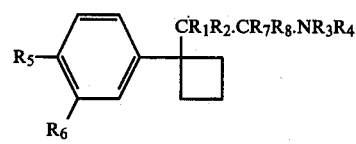

in which $R_5$ and $R_6$ are as defined above. In preferred compounds of formula II $R_5$ and $R_6$, which may be the same or different, are H, fluoro, chloro, bromo, iodo, trifluoromethyl, methyl (with the proviso that $R_5$ and $R_6$ cannot both be H or methyl) or $R_5$ and $R_6$ together with the carbon atoms to which they are attached form a second benzene ring.

A second group of preferred compounds of formula I is represented by formula III

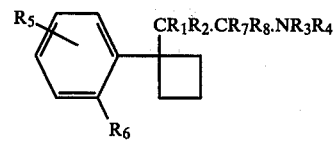

in which $R_5$ may be fluoro, chloro, bromo, iodo, trifluoromethyl, methyl and in which $R_6$ is fluoro In particularly preferred compounds of formula III $R_5$ is chloro.

In preferred compounds of formula I $R_7$ is H, methyl or ethyl and $R_8$ is H and in particularly preferred compounds of formula I $R_7$ is H or ethyl and $R_8$ is H.

Compounds of formula I may exist as salts with pharmaceutically acceptable acids. Examples of such salts include hydrochlorides, maleates, acetates, citrates, fumarates, tartrates, succinates and salts with acidic amino acids such as aspartic and glutamic acids.

Compounds of formula I which contain one or more asymmetric carbon atoms can exist in different optically active forms. When $R_1$ and $R_2$ are different or $R_7$ and $R_8$ are different, the compounds of formula I contain a chiral centre. Such compounds exist in two enantiomeric forms and the present invention includes both enantiomeric forms and mixtures thereof. When both $R_1$ and $R_2$ are different and $R_7$ and $R_8$ are different, the compounds of formula I contain two chiral centres and the compounds exist in four diastereoisomeric forms. The present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compounds are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat depression in mammals including human beings. In such treatment the amount of the compound of formula I administered per day is in the range 1 to 1000 mg preferably 5 to 500 mg.

Compounds of formula I may be prepared by the reductive amination of ketones or aldehydes of formula IV

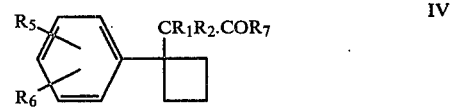

IV

Examples of suitable reductive amination processes are given below:

(a) for compounds of formula I in which $R_3$ and $R_4$ are H, by reaction of the ketone or aldehyde with an ammonium salt for example ammonium acetate and a reducing agent such as sodium cyanoborohydride.

(b) for compounds of formula I in which $R_3$ is alkyl or cycloalkyl and $R_4$ is H by reaction of the ketone or aldehyde with an amine of formula $R_3NH_2$ and a reducing agent such as sodium cyanoborohydride or sodium borohydride, (c) for compounds of formula I in which neither $R_3$ nor $R_4$ is hydrogen or in which $R_3$ and $R_4$ together with the nitrogen atom form a heterocyclic ring, by reaction of the ketone or aldehyde with an amine of formula $HNR_3R_4$ and either formic acid or a reducing agent such as sodiun cyanoborohydride.

(d) for compounds of formula I in which one or both of $R_3$ and $R_4$ are H or an alkyl or a cycloalkyl group or in which $R_3$ and $R_4$ together with the nitrogen atom form a heterocyclic ring, by catalytic hydrogenation at elevated temperature and pressure of a mixture of the ketone or aldehyde and an amine of formula $HNR_3R_4$.

Compounds of formula I in which $R_3$ and $R_4$ are both alkyl groups may be prepared by reacting ketones or aldehydes of formula IV with a dialkyl formamide of formula $HCONR_3R_4$ for example in the presence of formic acid.

Compounds of formula I may be prepared by the reduction of compounds of formula V

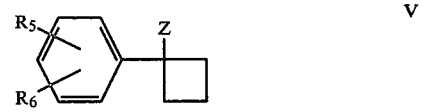

V in which (a) Z is a group of formula $-CR_1R_2.CN$ to give compounds of formula I in which $R_3$, $R_4$, $R_7$ and $R_8$ are H;

(b) Z is a group of formula $-CR_1R_2.CR_7=NOH$ or an ester or ether thereof to give compounds of formula I in which $R_3$, $R_4$ and $R_8$ are H;

(c) Z is a group of formula $-CR_1R_2.CR_7=NR_3$ to give compounds of formula I in which $R_4$ and $R_8$ are H;

(d) Z is a group of formula $-CR_1R_2.CR_7=NY$ in which Y represents a metal-containing moiety derived from an organometallic reagent to give compounds of formula I in which $R_3$, $R_4$ and $R_8$ are H;

(e) Z is a group of formula —$CR_1R_2.CONR_3R_4$ to give compounds of formula I in which $R_7$ and $R_8$ are H.

Suitable reducing agents for the above reactions include sodium borohyride, sodium cyanoborohydride, lithium aluminum hydride or borane-dimethylsulphide complex.

In (d) above Y is preferably MgBr derived from a Grignard reagent or Li derived from an organolithium compound.

Compounds of formula I may be prepared by the reaction of an organometallic reagent for example a Grignard reagent of formula $R_7MgX$ where X is Cl, Br or I or an organolithium compound of formula $R_7Li$ with imines of formula VI

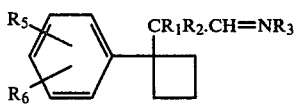

VI followed by hydrolysis to give secondary amines of formula I in which $R_8=H$.

Compounds of formula I in which $R_3$ and $R_4$ are H may be prepared by the decarboxylative rearrangement, for example using iodosobenzene-bistrifluoroacetate or by a Hofmann reaction using bromine in alkaline solution, of amides of formula VII

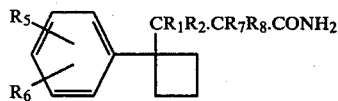

VII

Compounds of formula I in which $R_3$ and $R_4$ are H may be prepared by the decarboxylative rearrangement of acyl azides in the Curtius reaction. The acyl azides may be formed for example by reaction of acid chlorides of formula VIII with sodium azide.

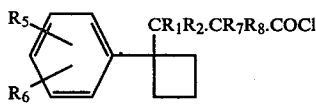

VIII

Compounds of formula I in which $R_3$ and $R_4$ are H may be prepared by a Schmidt reaction in which carboxylic acids of formula IX react with hydrazoic acid

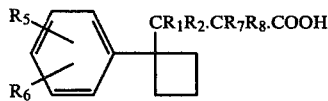

IX

Compounds of formula I in which $R_4$ is H may be prepared by hydrolysis of compounds of formula X for example by acid hydrolysis.

Compounds of formula I in which $R_4$ is methyl may be prepared by reduction of compounds of formula X for example by lithium aluminium hydride or by sodium bis(2-methoxyethoxy)aluminium hydride.

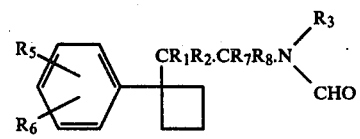

X

Compounds of formula X may be prepared by the reductive amidation of ketones or aldehydes of formula IV

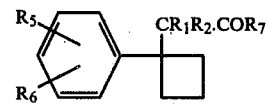

IV for example with formamide and formic acid or ammonium formate and formic acid to give compounds of formula X in which $R_3$ is H or with formamides of formula $HCONHR_3$ in which $R_3$ is an alkyl or cycloalkyl group and formic acid or amines of formula $R_3NH_2$ in which $R_3$ is an alkyl or cycloalkyl group and formic acid.

Compounds of formula I in which $R_3$ is other than H may be prepared by reacting compounds of formula X in which $R_3$ is H with a compound of formula $R_3X$ where X is a leaving group such as a halo group in the presence of a base.

Compounds of formula I in which one or both of $R_3$ and $R_4$ is other than H may be prepared from compounds of formula I in which one or both of $R_3$ and $R_4$ are hydrogen by methods which are well known in the art for the conversion of primary to secondary or tertiary amines or for the conversion of secondary to tertiary amines. The following are given as examples of suitable processes:

(a) by alkylating primary amines of formula I to give secondary amines of formula I for example by a process which includes the steps of protecting the primary amine with a protecting group such as trifluoroacetyl, alkylating with an alkyl halide and removing the protecting group for example by hydrolysis;

(b) by alkylating primary amines of formula I, for example, with an alkyl halide to give tertiary amines of formula I in which $R_3$ and $R_4$ are the same;

(c) by alkylating secondary amines of formula I, for example, with an alkylene halide to give tertiary amines of formula I in which $R_3$ and $R_4$ may be different;

(d) by reacting primary amines of formula I with sodium borohydride and acetic acid to give secondary amines of formula I in which $R_3$ is ethyl and $R_4$ is H;

(e) by reacting primary amines of formula I with formaldehyde and formic acid to give tertiary amines of formula I in which both $R_3$ and $R_4$ are methyl;

(f) by reacting secondary amines of formula I in which $R_4$ is H with formaldehyde and formic acid to give tertiary amines of formula I in which $R_4$ is methyl;

(g) by formylating primary amines of formula I, for example by reaction with methyl formate, and reducing the resulting formamides, for example with lithium aluminium hydride to give secondary amines of formula I in which $R_3$ is methyl and $R_4$ is H;

(h) by formylating secondary amines of formula I, for example by reaction with methyl formate, and reducing the resulting formamides, for example with lithium aluminium hydride to give tertiary amines of formula I in which $R_4$ is methyl.

(i) by acylating primary amines of formula I, for example by reaction with an acyl chloride of formula $R_{12}COCl$ or an anhydride of formula $(R_{12}CO)_2O$ in which $R_{12}$ is an alkyl, alkenyl or alkynyl group and reducing the resulting amides for example with lithium aluminium hydride to give secondary amines of formula I in which $R_3$ is $-CH_2R_{12}$ and $R_4$ is H.

(j) by acylating secondary amines of formula I in which $R_4$ is H for example by reaction with an acyl chloride of formula $R_{12}COCl$ or an anhydride of formula $(R_{12}CO)_2O$ in which $R_{12}$ is an alkyl, alkenyl or alkynyl group and reducing the resulting amides for example with lithium aluminium hydride to give tertiary amines in which $R_4$ is $CH_2R_{12}$;

(k) by reacting primary amines of formula I with an aldehyde of formula $R_{13}CHO$ in which $R_{13}$ may be an alkyl group, an alkenyl or alkynyl group or with a ketone of formula $R_{14}COR_{15}$ in which $R_{14}$ and $R_{15}$ which may be the same or different are an alkyl group, alkenyl group, alkynyl group or $R_{14}$ and $R_{15}$ together with carbon atom to which they are attached may form an alicyclic ring and reducing the resulting imines or enamines for example with sodium cyanoborohydride or, when $R_{13}$, $R_{14}$ or $R_{15}$ are not alkenyl or alkynyl, by catalytic hydrogenation to give secondary amines of formula I in which $R_3$ is $R_{13}CH_2-$ and

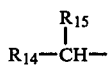

respectively;

(1) by reacting primary amines of formula I with a nongeminally disubstituted alkane containing 2 or 3 carbon atoms between the carbon atoms carrying the substituents which may be for example halo preferably bromo, or p-toluenesulphonyloxy to give compounds of formula I in which $R_3$ and $R_4$ together with the nitrogen to which they are attached form a heterocyclic ring containing no heteroatoms other than the nitrogen atom.

The ketones of formula IV may be prepared by the hydrolysis of imines of formula XI

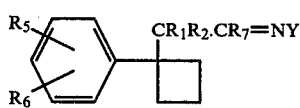

in which Y represents a metal-containing moiety derived from an organometallic reagent. The imines of formula XI may be prepared by the reaction of the said organometallic reagent with cyano compounds of formula XII

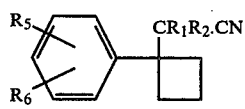

Suitable organometallic reagents include Grignard reagents of formula $R_7MgX$ where X is Cl, Br or I (Y=MgX) and organolithium compounds of formula $R_7Li$ (Y=Li).

Ketones of formula IV may be prepared by the reaction of carboxylic acid derivatives such as amides or acid halides with an organometallic reagent for example by the reaction of acid chlorides of formula XIII

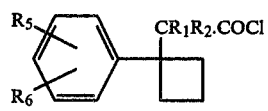

with a Grignard reagent of formula $R_7MgX$ where X is Cl, Br or I at low temperatures or by the reaction of carboxylic acids of formula XIV

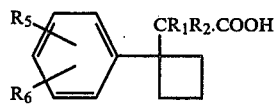

with an organometallic reagent, for example an organolithium compound of formula $R_7Li$.

Ketones of formula IV in which $R_7$ is alkyl (e.g. methyl) may be prepared by the reaction of a diazoalkane (e.g. diazomethane) with aldehydes of formula IV.

Aldehydes of formula IV may be prepared by methods well known in the art. The following are given as examples of suitable methods:

(a) by reduction of cyano compounds of formula XII with for example di-tert-butylaluminium hydride or di-isobutylaluminium hydride.

(b) by the reduction of carboxylic acid derivatives for example:
  (i) by reduction of compounds of formula V in which Z is $CR_1R_2.CONR_3R_4$ and $R_4$ are other than H for example by using lithium diethoxyaluminohydride.
  (ii) by reduction of amides formed by the reaction of ethyleneimine with acid chlorides of formula XII for example using lithium aluminium hydride.
  (iii) by the reduction of acid chlorides of formula XII for example with lithium tri-tert-butoxyaluminohydride.

(c) by the oxidation of alcohols (formed by the reduction of carboxylic acids of formula XIV) with, for example, chromium trioxide-pyridine complex in dichloromethane under anhydrous conditions.

Compounds of formula V in which Z is a group of formula $-CR_1R_2.CR_7=NOH$ or ethers or esters thereof may be prepared by the reaction of hydroxylamine or an ether or ester thereof with ketones or aldehydes of formula IV.

Compounds of formula V in which Z is a group of formula $-CR_1R_2.CR_7=NR_3$ may be prepared by the reaction of amines of formula $R_3NH_2$ with ketones or aldehydes of formula IV.

The preparation of compounds of formula V in which Z is a group of formula $-CR_1R_2.CR_7=NY$ has been described above in respect of compounds of formula XI.

The preparation of compounds of formula V in which Z is a group of formula $-CR_1R_2.CN$ will be described hereinafter in respect of the cyano compounds of formula XII.

Compounds of formula V in which Z is a group of formula $-CR_1R_2.CONR_3R_4$ may be prepared by the reaction of acid derivatives such as esters or acid halides (for example acid chlorides of formula XIII) with amines of formula $HNR_3R_4$ or ammonia. Compounds of formula V in which Z is $CR_1R_2.CONH_2$ may be prepared from cyano compounds of formula XII for example by hydration, with aqueous acids or by reaction with hydrogen peroxide in the presence of a base.

Imines of formula VI may be prepared by reaction of amines of formula $R_3NH_2$ with aldehydes of formula IV.

Amides of formula VII may be prepared by the reaction of ammonia with carboxylic acid derivatives for example acid chlorides of formula VIII or they may be prepared from cyano compounds of formula XV for example by hydration with aqueous acids or by reaction with hydrogen peroxide in the presence of a base.

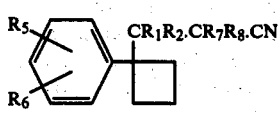
XV

Amides of formula VII in which $R_7$ and $R_8$ are H and amides of formula XVI in which $R_1$ and $R_2$ are H

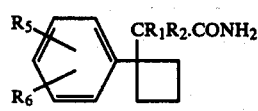
XVI may be prepared from acid chlorides of formula XIII and XVII respectively

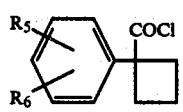
XVII by reaction with diazomethane to form diazoketones which rearrrange in the presence of ammonia and a catalyst for example silver to give the required amides.

Carboxylic acids of formula XIV and IX may be prepared by the hydrolysis, for example basic hydrolysis, of cyano compounds of formula XII and XV respectively. Carboxylic acids of formula XIV and IX may be prepared by the reaction of amides of formula XVI and VII respectively with nitrous acid.

Carboxylic acids of formula XIV in which $R_1$ and $R_2$ are H and carboxylic acids of formula IX in which $R_7$ and $R_8$ are H may be prepared from acid chlorides of formula XVII and XIII respectively by reaction with diazomethane to form diazoketones which rearrange in the presence of water and a catalyst for example silver to give the required acids.

Cyano compounds of formula XII in which $R_1$ and $R_2$ are H may be prepared from cyano compounds of formula XVIII

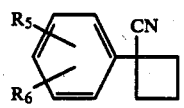
XVIII by for example the following series of reactions:

(a) hydrolysis of the cyano group to form a carboxylic acid of formula XIX

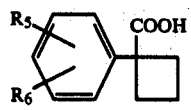
XIX (b) reduction of the carboxylic acid for example with lithium aluminium hydride or borane-dimethylsulphide complex to form the corresponding alcohol;

(c) replacement of the hydroxy group of the alcohol by a leaving group for example p-toluene sulphonyloxy group and (d) replacement of the leaving group with a cyano group. In a similar manner cyano compounds of formula XV may be prepared from cyano compounds of formula XII.

Cyano compounds of formula XII in which one or both of $R_1$ and $R_2$ are other than H may be prepared from the corresponding cyano compounds of formula XII in which $R_1$ and/or $R_2$ are H, for example by alkylation with an alkyl halide in the presence of a base such as lithium diisopropylamide. In a similar way cyano compounds of formula XV in which one or both of $R_7$ and $R_8$ are other than hydrogen may be prepared from compounds of formula XV in which $R_7$ and $R_8$ are both H.

Cyano compounds of formula XII in which $R_2=H$ may also be prepared by reacting ketones of formula XX

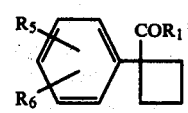
XX or aldehydes of formula XXI

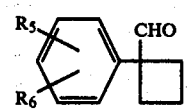
XXI with a reagent for introducing a cyano group such as p-toluenesulphonylmethyl isocyanide. In a similar manner cyano compounds of formula XV may be prepared from aldehydes or ketones of formula IV.

Cyano compounds of formula XVIII may be prepared by the reaction of cyano compounds of formula XXII

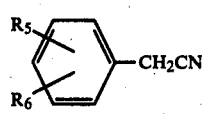
XXII with a 1,3-disubstituted propane for example 1,3-dibromopropane and a base such as sodium hydride.

Acid chlorides of formula XVII, XIII and VIII may be prepared by the reaction of carboxylic acids of formula XIX, XIV and IX respectively with for example thionyl chloride.

The ketones of formula XX may be prepared by the hydrolysis of imines of formula XXIII

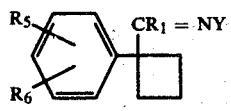

in which Y represents a metal-containing moiety derived from an organometallic reagent. The imines of formula XXIII may be prepared by the reaction of said organometallic reagent with cyano compounds of formula XVIII. Suitable organometallic reagents include Grignard reagents of formula $R_1MgX$ where X is Cl, Br or I (Y=MgX) and organolithium compounds of formula $R_1Li$ (Y=Li).

Ketones of formula XX may be prepared by the reaction of carboxylic acid derivatives such as amides or acid halides with an organometallic reagent, for example by the reaction of acid chlorides of formula XVII with a Grignard reagent of formula $R_1MgX$ where X is Cl, Br or I at low temperatures or by the reaction of carboxylic acids of formula XIX with for example an organolithium compound of formula $R_1Li$.

Aldehydes of formula XXI may be prepared by methods well known to those skilled in the art. The following are given as examples of suitable methods:
(a) by the reduction of cyano compounds of formula XVIII with for example di-tert-butylaluminium hydride or diisobutylaluminium hydride.
(b) by the reduction of carboxylic acid derivatives, for example
  (i) by the reduction of tertiary amides formed by the reaction of secondary amines with acid chlorides of formula XVII for example when the secondary amine is a dialkylamine using lithium diethoxyaluminohydride as reducing agent or when the secondary amine is ethyleneimine using lithium aluminium hydride as the reducing agent,
  (ii) by the reduction of acid chlorides of formula XVII for example with lithium tri-tert-butoxyaluminohydride.
(c) by the oxidation of alcohols (prepared by the reduction of carboxylic acids of formula XIX with, for example, chromium trioxide-pyridine complex in dichloromethane under anhydrous conditions.

Ketones of formula IV, aldehydes of formula IV, the compounds of formula V, the imines of formula VI, the amides of formula VII, the carboxylic acids of formula XIV and IX, the cyano compounds of formula XII and XV and the acid chlorides of formula XIII and VIII which are described herein as intermediates are novel compounds. Such novel compounds form a further aspect of the present invention.

Novel formamides of formula X

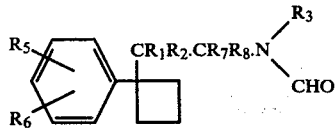

are described herein as intermediates, in the preparation of compounds of formula I and such novel formamides form a further aspect of the present invention.

The therapeutic activity of the compounds of formula I has been indicated by assessing the ability of the compounds to reverse the hypothermic effects of reserpine in the following manner. Male mice of the Charles River CD1 strain weighing between 18 and 30 grammes were separated into groups of five and were supplied with food and water ad libitum. After five hours the body temperature of each mouse was taken orally and the mice were injected intraperitoneally with reserpine (5 mg/kg) in solution in deionised water containing ascorbic acid (50 mg/ml). The amount of liquid injected was 10 ml/kg of body weight. Nine hours after the start of the test food was withdrawn but water was still available ad libitum. Twenty-four hours after the start of the test the temperatures of the mice were taken and the mice were given the test compound suspended in a 0.25% solution of hydroxy ethyl cellulose (solid under the trade name Cellosize QP 15000 by Union Carbide) in deionised water at a dose volume of 10 ml/kg of body weight. Three hours later the temperatures of all the mice were again taken. The percentage reversal of the reserpine-induced loss of body temperature is then calculated by the formula:

$$\frac{(\text{Temperature after 27 hrs} - \text{Temperature after 24 hours}) \times 100}{(\text{Temperature after 5 hrs} - \text{Temperature after 24 hours})}$$

The mean value for each group of five mice was taken at several does rates to enable a value of the mean dose which causes a 50% reversal (ED50) to be obtained. All the compounds which are the final products of the Examples hereinafter gave values of ED50 of 30 mg/kg or less. It is widely understood by those skilled in the art that this test is indicative of compounds having antidepressant activity in humans.

The invention will now be illustrated by the following Examples which are given by way of example only. All compounds were characterised by conventional analytical techniques and gave satisfactory elemental analyses. All melting and boiling points are expressed in degrees Celsius.

EXAMPLE 1

A solution of 4-chlorobenzyl cyanide (10 g) and 1,3-dibromopropane (7.5 ml) in dry dimethyl sulphoxide (12 ml) was added dropwise under nitrogen to a stirred mixture of sodium hydride (3.6 g) dispersed in mineral oil (3,6 g) and dimethylsulphoxide (70 ml) at a temperature in the range 30° to 35° C. The mixture was stirred at room temperature for two hours and then propan-2-ol (10 ml) and water (150 ml) were added dropwise. The mixture was filtered through a diatomaceous earth sold under the Registered Trade Mark CELITE and the solid residue washed with ether. The filtrate was extracted with ether and the ether phases combined, washed with water, dried and evaporated. 1-(4-chlorophenyl)-1-cyclobutanecarbonitrile (b.p. 116°–120° at 0.6 mm Hg) was isolated by distillation. This method is a modification of that described by Butler and Pollatz (J.Org.Chem., Vol. 36, No. 9, 1971, p. 1308).

1-(4-Chlorophenyl)-1-cyclobutanecarbonitrile (37.6 g) prepared as described above was added to a solution of potassium hydroxide (32.4 g) in diethyleneglycol (370 ml) and the mixture heated under reflux for three and a half hours. The reaction mixture was poured into an ice/water mixture and the resulting solution was washed with ether. The aqueous layer was added to a mixture of concentrated hydrochloric acid (100 ml) and ice and the resulting precipitate of 1-(4-chlorophenyl)-1-cyclobutanecarboxylic acid (m.p. 86°–88° C.) collected, washed with water and dried.

A solution of the acid (10.5 g) prepared as above in tetrahydrofuran (150 ml) was added dropwise under nitrogen to a stirred suspension of lithium aluminium hydride (2 g) in tetrahydrofuran (150 ml). The mixture was stirred under reflux for two hours and water added. The mixture was filtered through diatomaceous earth (CELITE-RTM) and the product extracted into ether. After washing with water and drying, the ether was evaporated to give a residue which was recrystallised from petroleum ether (b.p. 60°–80°). The product was 1-[1-(4-chlorophenyl)cyclobutyl]methyl alcohol (m.p. 60°–62° C.).

A solution of the alcohol prepared as described above (60 g) in pyridine (52 ml) was added dropwise to a solution of p-toluenesulphonylchloride (60 g) in pyridine (100 ml) cooled in ice. The temperature was allowed to rise to room temperature and remain there for eighteen hours. 1-[1-(4-Chlorophenyl)cyclobutyl]methyl p-toluene sulphonate (m.p. 99°–100° C.) was precipitated by pouring the reaction mixture into a mixture of ice and concentrated hydrochloric acid (200 ml).

A solution of the sulphonate compound (97 g) prepared as described above and sodium cyanide (16.6 g) in dimethyl sulphoxide (370 ml) was heated on a steam bath for eighteen hours. The mixture was poured into water and extracted with ether. After washing and drying the ether was evaporated to leave a solid residue of 2-[1-(4-chlorophenyl)-cyclobutyl]acetonitrile (m.p. 63°–65° C.).

The acetonitrile prepared above (20 g) was dissolved in ether (120 ml) and the solution added dropwise under nitrogen to a stirred suspension of lithium aluminium hydride (5.84 g) in ether (80 ml). The mixture was stirred at ambient temperature for one and a half hours and then under reflux for a further two hours. Water was added dropwise and the resulting mixture filtered through diatomaceous earth. The residue was washed with ether. The filtrate was extracted with ether and the combined ether portions were washed with water and extracted with 5 N hydrochloric acid. The acid solution was washed with ether and aqueous NaOH was added. The product was extracted into ether and the extract washed with water, dried and evaporated to give a residue which on distillation gave 2-[1-(4-chlorophenyl)cyclobutyl]ethylamine (b.p. 119°–121°/1.5 mm Hg).

The ethylamine prepared as described above (6.9 g), 98% formic acid (6.6 ml), water (0.9 g) and 37 to 40% aqueous formaldehyde solution (9 ml) were heated on a steam bath for eighteen hours. The mixture was cooled and excess concentrated hydrochloric acid added. A yellow solid residue was obtained on evaporation to dryness. The solid was partitioned with dichloromethane and 5 N sodium hydroxide solution and the aqueous layer extracted with a further portion of dichloromethane. The dichloromethane portions were combined, washed with water, dried and evaporated to yield a solid residue which was dissolved in propan-2-ol (15 ml) and concentrated hydrochloric acid was added to pH 2. The mixture was evaporated to dryness and the residue recrystallised from ethyl acetate to give colourless crystals of N,N-dimethyl-2-[1-(4-chlorophenyl)cyclobutyl]ethylamine hydrochloride (m.p. 220°–222° C.) (Formula 1 R$_1$, R$_2$=H; R$_3$, R$_4$=Me; R$_5$=4-Cl; R$_6$, R$_7$ and R$_8$=H).

In a similar manner to that described above the following compounds were made

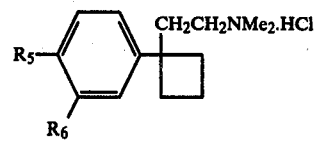

| Example | R$_5$ | R$_6$ | m.p. of HCl salt |
|---|---|---|---|
| 1(a) | Cl | Cl | 218–220° |
| 1(b) | I | H | 263–265° |
| 1(c) | —CH=CH—CH=CH— | | 234–236° |
| 1(d) | In a similar manner N,N—dimethyl-2-[1-(4-chloro-2-fluorophenyl)cyclobutyl]ethylamine hydrochloride (m.p. 232–233° C. (dec)) was prepared. | | |

EXAMPLE 2

2-[1-(4-Chlorophenyl)cyclobutyl]ethylamine (12 g) prepared as described in Example 1, 1,4-dibromobutane (12.4 g) and anhydrous sodium carbonate (14.3 g) were mixed in xylene (100 ml) and the mixture heated under reflux with stirring for sixteen hours. The mixture was cooled, filtered and the xylene removed by evaporation to give a residue which on distillation gave N-2-[1-(4-chlorophenyl)cyclobutyl]ethylpyrrolidine (b.p. 148°–150°/1.5 mm Hg) (Formula 1 R$_1$, R$_2$=H; R$_3$ and R$_4$ together with the nitrogen atom forming a pyrrolidine ring; R$_5$=4-Cl; R$_6$, R$_7$ and R$_8$=H).

In a similar manner to that described above the following compounds were made and isolated as their hydrochloride salts.

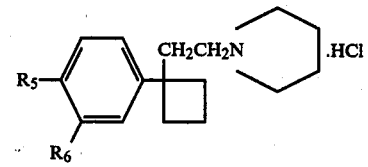

| Example | R$_5$ | R$_6$ | m.p. of HCl salt |
|---|---|---|---|
| 2(a) | Cl | Cl | 213° |
| 2(b) | —CH=CH—CH=CH— | | 232–233° |

EXAMPLE 3

A solution of 2-[1-(4-chlorophenyl)cyclobutyl]acetonitrile (30 g) prepared as described in Example 1 in ether (100 ml) was added to the reaction product of methyl bromide gas and magnesium turnings (5.95 g) in ether (80 ml). The mixture was heated under reflux for four hours. Ice and then concentrated hydrochloric acid (105 ml) were added and the mixture heated under reflux until all solid material had dissolved. The aqueous layer was washed with ether and the ether used for washing was combined with the ether phase of the reaction mixture. The combined ether extracts were washed with water, dried and evaporated to yield a residue which was distilled twice to yield 1-[1-(4-chlorophenyl)cyclobutyl]propan-2-one (b.p. 133°–136°/2.5 mm Hg).

The ketone prepared as described above (5.4 g) was mixed with N-methylformamide (18 ml), 98% formic acid (4 ml) and 25% aqueous methylamine (0.6 ml) and the mixture heated under reflux for sixteen hours. The mixture was poured into water and extracted with dichloromethane. The extract was washed, dried and evaporated to give a residue which was heated under reflux with concentrated hydrochloric acid (10 ml) for six hours. The mixture was evaporated to dryness and the residue dried by repeated addition and vacuum evaporation of an industrial methylated spirit/toluene mixture. The solid residue was recrystallised from propan-2-ol to give N-methyl-2-[1-(4-chlorophenyl)cyclobutyl]-1-methylethylamine hydrochloride (m.p. 193°-194° C.) (Formula I $R_1$, $R_2$=H; $R_3$=Me; $R_4$=H; $R_5$=4-Cl; $R_6$=H; $R_7$=Me; $R_8$=H).

EXAMPLE 4

A mixture of 1-[1-(4-chlorophenyl)cyclobutyl]propan-2-one prepared as described in Example 3 (15 g) and 98% formic acid (4 ml) was added dropwise to formamide (12 ml) at 160° C. The temperature was raised to 180° C. and maintained at this temperature for ten hours. The mixture was cooled, diluted with water and extracted with dichloromethane. The extract was washed, dried and evaporated to yield a yellow oil which was hydrolysed with concentrated hydrochloric acid under reflux. The resulting aqueous solution after dilution with water was washed with ether, aqueous NaOH was added and the aqueous solution extracted with ether. The extracts were washed, dried and evaporated to yield a residue which on distillation gave 2-[1-(4-chlorophenyl)cyclobutyl]-1-methylethylamine (b.p. 105°-107°/0.7 mm Hg).

The amine obtained above (2.65 g) was dissolved in propan-2-ol (15 ml) and concentrated hydrochloric acid added dropwise until the pH was 2. Ether (110 ml) was added and colourless crystals of 2-[1-(4-chlorophenyl)cyclobutyl]-1-methylethylamine hydrochloride (m.p. 184°-185° C.) were collected. (Formula I $R_1$, $R_2$=H; $R_3$, $R_4$=H; $R_5$=4-Cl; $R_6$=H; $R_7$=Me and $R_8$=H).

EXAMPLE 5

2-[1-(4-Chlorophenyl)cyclobutyl]-1-methylethylamine (3.94 g) prepared as described in Example 4, 1,4-dibromobutane (3.82 g), anhydrous sodium carbonate (4.4 g) and xylene (30 ml) were mixed and heated under reflux for sixteen hours. The mixture was cooled, filtered and evaporated to yield a residue which was distilled twice (b.p. 130°-132°/0.5 mm Hg). The product of the distillation was dissolved in propan-2-ol (5 ml) and ether (70 ml) and concentrated hydrochloric acid added to pH 2. The solution was evaporated in vacuo and the residue recrystallised from ethyl acetate to give N-{2-[1-(4-chlorophenyl)cyclobutyl]-1-methyl}ethylpyrrolidine hydrochloride (m.p. 151°-152° C.) (Formula I $R_1$,$R_2$=H; $R_3$ and $R_4$ together with the nitrogen atom forming a pyrrolidine ring; $R_5$=4-Cl; $R_6$=H; $R_7$=Me; $R_8$=H).

EXAMPLE 6

1-[1-(4-chlorophenyl)cyclobutyl]propan-2-one prepared as described in Example 3 (25 g) and 98% formic acid (10 ml) were added to formamide (22 ml) at 160° C. The temperature was raised to 175° C. and maintained at this temperature for sixteen hours. The mixture was cooled, extracted with dichloromethane. The extract was washed with water and evaporated to give a gum which was crystallised from petroleum ether (b.p. 40°-60° C.) to give N-formyl-2-[1-(4-chlorophenyl)cyclobutyl]-1-methylethylamine (m.p. 71°-73° C.).

N-formyl-2-[1-(4-chlorophenyl)cyclobutyl]-1-methylethylamine (11.06 g) prepared as described above was heated under reflux for six hours with a mixture of concentrated hydrochloric acid (34 ml) water (34 ml) and diethyleneglycoldimethyl ether (40 ml). The mixture was cooled, washed with ether and basified with aqueous sodium hydroxide. The basified solution was extracted into ether, washed with water, dried, evaporated and distilled to give 2-[1-(4-chlorophenyl)cyclobutyl]-1-methylethylamine (b.p. 119°-121° C. at 0.8 mm Hg). The amine (2.65 g) was dissolved in propan-2-ol (15 ml) and concentrated hydrochloric acid added to pH 2. Ether (110 ml) was added and crystals of 2-[1-(4-chlorophenyl) cyclobutyl]-1-methylethylamine hydrochloride (m.p. 184°-185° C.) were collected. (Formula I $R_1$, $R_2$=H; $R_3$, $R_4$=H; $R_5$=4-Cl; $R_6$=H; $R_7$=Me and $R_8$=H.)

EXAMPLE 7

2-[1-(4-Chlorophenyl)cyclobutyl]-1-methylethylamine (1.8 g) prepared as described in Example 6 was mixed with formic acid (4.5 ml). 37 to 40% Aqueous formaldehyde solution (6 ml) was added and the mixture heated first at 45°-50° C. for 30 minutes and then under reflux for two hours. The mixture was cooled, basified with aqueous sodium hydroxide, extracted with ether, the ether extract was washed with water and extracted with 5 N hydrochloric acid. The acid extract with washed with ether, basified with aqueous sodium hydroxide, and extracted with ether. Hydrogen chloride gas was passed through the ether extract and a white solid was formed. The solid was collected and recrystallised from ethyl acetate to give N,N-dimethyl-2-[1-(4-chlorophenyl)cyclobutyl]-1-methylethylamine hydrochloride (m.p. 108°-110° C.) (Formula I $R_1$, $R_2$=H; $R_3$, $R_4$=Me; $R_5$=4-Cl; $R_6$=H; $R_7$=Me; $R_8$=H).

EXAMPLE 8

A 70% solution of sodium bis(2-methoxyethoxy) aluminum hydride in toluene (sold under the trade mark Red-al) (35 ml) was added dropwise to a solution of N-formyl-2-[1-(4-chlorophenyl)cyclobutyl]-1-methylethylamine prepared as described in Example 6 (5 g) in dry ether (110 ml) with cooling to maintain the temperature at less than 10° C. The temperature was allowed to rise to about 25° C. and then the mixture was heated under reflux for two hours. The reaction mixture was poured into a mixture of crushed ice and concentrated hydrochloric acid. The resulting mixture was washed with ether, basified with aqueous sodium hydroxide and extracted with ether. The ether extract was washed with brine, dried and evaporated to give a liquid which was dissolved in petroleum ether (b.p. 40°-60° C.). Hydrogen chloride gas was bubbled through the solution to precipitate a solid which was recrystallised from propan-2-ol to give N-methyl-2-[1-(4-chlorophenyl)cyclobutyl]-1-methylethylamine hydrochloride (Formula I $R_1$, $R_2$=H; $R_3$=H; $R_4$=Me; $R_5$=4-Cl; $R_6$=H; $R_7$=Me and $R_8$=H) (m.p. 192°-194° C.).

EXAMPLE 9

A solution in ether (80 ml) of 2-[1-(3,4-dichlorophenyl)cyclobutyl]acetonitrile (23 g) prepared in a similar manner to that described in Example 1 for 2-[1-(4-chlorophenyl)cyclobutyl]acetonitrile was added to the product of the reaction between magnesium turnings (3.53 g) and ethyl bromide (10.8 ml) in dry ether (80 ml) with stirring whilst heating on a steam bath. The ether was removed and replaced with toluene and the mixture heated under reflux for one hour. Water was added and the mixture added to a mixture of ice and concentrated hydrochloric acid. The mixture was heated on a steam bath for one hour and filtered through a diatomaceous earth sold under the Registered Trade Mark CELITE. The filtrate was extracted with dichloromethane and the extract washed with water and sodium bicarbonate solution and dried. The solvent was removed by evaporation and the residue distilled to give 1-[1-(3,4-dichlorophenyl)cyclobutyl]butan-2-one (b.p. 149°-150°/1.1 mm Hg).

The ketone prepared as above was converted into 1-{[1-(3,4-dichlorophenyl)cyclobutyl]methyl}propylamine hydrochloride (m.p. 225°-226° C.) (Formula I $R_1$, $R_2$, $R_3$, $R_4$=H; $R_5$=4-Cl; $R_6$=3-Cl; $R_7$=Et; $R_8$=H) in a similar manner to that described in Example 6.

In a similar manner to that described above 2-[1-(3,4-dichlorophenyl)cyclobutyl]-1-methylethylamine hydrochloride (m.p. 179° C.) (Example 9 a Formula I $R_1$, $R_2$, $R_3$ and $R_4$=H; $R_5$=4-Cl; $R_6$=3-Cl; $R_7$=Me and $R_8$=H) was prepared.

EXAMPLE 10

In a similar manner to that described in Example 7 compounds prepared in a similar manner to that described in Example 9 were converted into the corresponding N,N-dimethyl compounds.

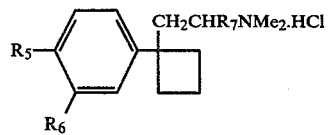

| Example | Starting Material | $R_5$ | $R_6$ | $R_7$ | m.p. |
|---|---|---|---|---|---|
| 10(a) | 9 | Cl | Cl | Et | 177-178° |
| 10(b) | 9(a) | Cl | Cl | Me | 204-205° |

EXAMPLE 11

In a similar manner to that described in Example 8, N-formyl compounds prepared as described in Example 6 from ketones prepared as in Example 9 were converted into the corresponding N-methyl compounds.

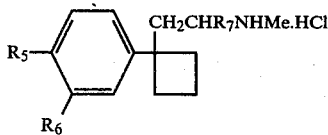

| Example | $R_5$ | $R_6$ | $R_7$ | m.p. |
|---|---|---|---|---|
| 11(a) | Cl | H | Et | 170-172° |
| 11(b) | Cl | Cl | Et | 193-194° |

EXAMPLE 12

A mixture of 2-[1-(4-chlorophenyl)cyclobutyl]acetonitrile (10.1 g) prepared as described in Example 1, potassium hydroxide (8.1 g) and diethyleneglycol (92 ml) was heated under reflux for three and a half hours. The mixture was poured into an ice/water mixture and the resulting solution washed three times with ether and added to a mixture of ice and concentrated hydrochloric acid. On cooling a solid product separated which was recrystallised from petroleum ether (b.p. 62°-68° C.) with the use of charcoal. The recrystallised product was 2-[1-(4-chlorophenyl)cyclobutyl]acetic acid (m.p. 83°-84° C.).

The acid (5 g) prepared as described above was added to thionyl chloride (20 ml) and heated under reflux for one hour. Excess thionyl chloride was then removed and the residue poured into a solution of piperidine (3.8 g) in ether (20 ml). The mixture was stirred for thirty minutes and then water was added to dissolve piperidine hydrochloride. The ether layer was separated and the aqueous layer washed with ether. The combined ether portions were washed with water, dried and evaporated to yield a brown oil which was purified by distillation (b.p. 168°/1 mm Hg) and crystallisation from petroleum ether (b.p. 40°-60° C.). The solid product was N-2-[1-(4-chlorophenyl)cyclobutyl]acetylpiperidine (m.p. 66°-67° C.).

A solution of the compound prepared as described above (2.7 g) in ether (20 ml) was added dropwise to a stirred mixture of lithium aluminum hydride (0.7 g) and ether under a nitrogen atmosphere. Stirring was continued for one hour at room temperature and then during heating under reflux for two hours. After cooling in ice, excess lithium aluminum hydride was decomposed by the addition of water. The mixture was filtered through diatomaceous earth (CELITE). The aqueous portion of the filtrate was washed with a portion of ether and this portion was combined with ether portions which had been used to wash the solid residue. The combined ether portions were washed with water, dried and evaporated. The residue was purified by distillation. The product was N-2-[1-(4-chlorophenyl)cyclobutyl]ethylpiperidine (b.p. 152°-156°/1.5 mm Hg) (Formula $R_1$, $R_2$=H; $R_3$ and $R_4$ together with the nitrogen atom forming a perididine ring; $R_5$=4-Cl; $R_6$, $R_7$ and $R_8$=H).

In a similar manner to that described above the following compounds were made and isolated as their hydrochloride salts by bubbling dry hydrogen chloride gas through a solution of the base in petroleum ether (b.p. 62°-68° C.).

| Example | $R_5$ | $R_6$ | $NR_3R_4$ | m.p. (°C.) |
|---|---|---|---|---|
| 12(a) | Cl | H | Me—N(piperidine)—Me | 167-169° |
| 12(b) | Cl | H | —N(piperazine)N—Me | 281-283° (dec) |
| 12(c) | Cl | H | —N(tetrahydropyridine) | 246-248° |

EXAMPLE 13

1-(4-Chlorophenyl)-1-cyclobutanecarbonitrile (Example 1) (36.4 g) was dissolved in dry ether (100 ml) and the solution was added under nitrogen to the product of the reaction of gaseous methyl bromide with magnesium turnings (7.75 g) in dry ether (100 ml). The mixture was stirred at room temperature for two hours and then under reflux for two hours. Crushed ice and then concentrated hydrochloric acid (140 ml) were added and the mixture heated under reflux for 20 hours. The ether layer was separated, washed with water, aqueous sodium bicarbonate, dried and evaporated. 1-Acetyl-1-(4-chlorophenyl)cyclobutane (b.p. 88°–90° at 0.2 mm Hg) was isolated by distillation.

A mixture of sodium hydride (9 g), mineral oil (9 g) and dry dimethylformamide (150 ml) was stirred under nitrogen at 0° C. A solution of p-toluenesulphonylmethyl isocyanide which is sold under the trade name TosMIC (24.6 g) in dimethylformamide (50 ml) was added over twenty minutes. Absolute alcohol (18 g) was then added to the mixture at 0° C. over a period of one hour. 1-Acetyl-1-(4-chlorophenyl)cyclobutane (24 g) prepared as described above dissolved in dry dimethylformamide (20 ml) was added and the mixture was stirred for sixteen hours during which the temperature rose to ambient temperature. The mixture became viscous and petroleum ether (b.p. 80°–100° C.) (25 ml) was added. The mixture was poured into water and the pH adjusted to 6 by the addition of 5 N hydrochloric acid. The resulting mixture was extracted with ether and the ether extract washed with water, dried and partially evaporated. A brown solid separated and was removed by filtration and the filtrate was evaporated and 2-[1-(4-chlorophenyl)cyclobutyl]propionitrile (b.p. 128°–136°/0.6 mm) collected by distillation.

A solution of the propionitrile prepared as described above (3.5 g) in dry ether (20 ml) was added dropwise to a stirred mixture of lithium aluminium hydride (0.9 g) in dry ether (20 ml) at a temperature in the range 15° to 20° C. The mixture was stirred at ambient temperature for two hours and then during heating under reflux for a further three hours. 5 N Sodium hydroxide solution (20 ml) and water (50 ml) were added and the mixture filtered through diatomaceous earth (CELITE). The filter medium was washed with ether and the washings combined with the ether of the reaction mixture. The combined extracts were extracted with 5 N hydrochloric acid. A solid formed at the interface which was collected by filtration, washed with acetone and dried. The solid was 2-[1-(4-chlorophenyl)cyclobutyl]propylamine hydrochloride (m.p. 210°–230° C.).

The hydrochloride salt (1.0 g) prepared as above was dissolved in water, 5 N aqueous sodium hydroxide solution was added and the solution extracted with ether. The ether extract was dried and evaporated to yield an oil which was heated under reflux for six hours with 1,4-dibromobutane (0.82 g), anhydrous sodium carbonate (0.96 g) and xylene (6.5 ml). The mixture was cooled, filtered through diatomaceous earth (CELITE) and evaporated to dryness. The residue was dissolved in propan-2-ol (10 ml) and concentrated hydrochloric acid (5 ml) added. The mixture was evaporated to dryness and the residue collected, washed with ether and dried. The product was N-2-[1-(4-chlorophenyl)cyclobutyl]propylpyrrolidine hydrochloride (m.p. 238°–248° C.) (Formula I $R_1$=Me; $R_2$=H; $R_3$ and $R_4$ together with the nitrogen to which they are attached forming a pyrrolidine ring; $R_5$=4-Cl; $R_6$, $R_7$ and $R_8$=H).

EXAMPLE 14

A solution of 1-(3,4-dichlorophenyl)-1-cyclobutane carbonitrile (70 g) prepared in a similar manner to that described in Example 1 in industrial methylated spirit (200 ml) was mixed with a solution of sodium hydroxide (3.7 g) in water (5 ml) and 30% hydrogen peroxide solution added dropwise. The mixture was heated at 50° C. for one hour and then stirred with 10% palladium on charcoal (0.5 g) for one hour. The mixture was filtered and evaporated to dryness to give 1-(3,4-dichlorophenyl)-1-cyclobutane-carboxamide.

The carboxamide prepared above was dissolved in dioxane (500 ml) and concentrated hydrochloric acid (100 ml) and then a solution of sodium nitrite (35 g) in water (80 ml) were added dropwise. The mixture was heated at 85° to 95° C. for sixteen hours and then poured into water. The mixture was extracted with ether and the extract back-extracted with aqueous potassium carbonate. The basic extract was washed with ether and acidified with concentrated hydrochloric acid to give 1-(3,4-dichlorophenyl)-1-cyclobutanecarboxylic acid (m.p. 120°–121° C.).

The acid prepared as above was converted into the compound of Example 1(a) in a similar manner to that described in Example 1 and to the compound of Example 2(a) in a similar manner to that described in Example 2.

EXAMPLE 15

A solution of 2-[1-(3,4-dichlorophenyl)cyclobutyl]acetonitrile (23 g prepared in a similar manner to 2-[1-(4-chlorophenyl)cyclobutyl]acetonitrile described in Example 1) in dry ether (50 ml) was added to a solution of ethyl magnesium bromide prepared by the dropwise addition of ethyl bromide (15.83 g) in dry ether (80 ml) to a stirred mixture of magnesium turnings (3.53 g) and ether (80 ml). The mixture was heated under reflux for 30 minutes and stirred without further heating for 16 hours and then under reflux for a further two hours. 1-[1-(3,4-dichlorophenyl)cyclobutyl]-2-butanimine bromomagnesium salt was collected by filtration and a sample of the solid (about 1 g) was added to a solution of sodium borohydride (3 g) in diethyleneglycoldimethyl ether (30 ml). The mixture was stirred at 45° C. for 90 minutes. The reaction mixture was extracted with 5 N hydrochloric acid. The aqueous phase was basified with aqueous sodium hydroxide solution and extracted with ether. The ether extract was dried and hydrogen chloride gas passed into the extract to precipitate 1-{[1-(3,4-dichlorophenyl)cyclobutyl]methyl}-propylamine hydrochloride (m.p. 223°–224° C.) (Formula I $R_1$, $R_2$, $R_3$ and $R_4$=H; $R_5$=4-Cl; $R_6$=3-Cl; $R_7$=Et; $R_8$=H).

EXAMPLE 16

Formic acid (7 ml) was added dropwise to pyrrolidine (15 ml) at a temperature in the range 135°–140° C. 1-[1-(3,4-dichlorophenyl)cyclobutyl]butan-2-one (3 g) prepared as described in Example 9 was added dropwise and the mixture heated at 140° C. for one hour. The temperature was raised to 185°–190° C. for sixteen hours. The reaction mixture was cooled and poured into 5 N hydrochloric acid. The solution was washed with ether, basified and extracted with ether. The ether extract was dried and hydrogen chloride gas passed into the extract. Evaporation to dryness gave a solid which was triturated with dry ether and recrystallised from a mixture of petroleum ether and propan-2-ol to give N-1-{1-(3,4-dichlorophenyl)cyclobutyl]methyl}propyl-pyrrolidine hydrochloride (m.p. 157°–160° C.) (Formula I $R_1$, $R_2$=H; $R_3$ and $R_4$ together with the nitrogen atom forming a pyrrolidine ring; $R_5$=4-Cl; $R_6$=3-Cl; $R_7$=Et and $R_8$=H).

EXAMPLE 17

1-[1-(3,4-dichlorophenyl)cyclobutyl]-2-butanimine bromo-magnesium salt (25 g) prepared as described in Example 15 was heated at 90°–95° C. for two hours with a mixture of concentrated hydrochloric acid (20 ml) and water (30 ml). The reaction mixture was extracted with ether and the ether extract dried and evaporated to dryness. 1-[1-(3,4-dichlorophenyl)cyclobutyl]butan-2-one (b.p. 122°–124° at 0.1 mm Hg) was distilled.

A mixture of 1-[1-(3,4-dichlorophenyl)cyclobutyl]butan-2-one (4.3 g) prepared as described above, hydroxylamine sulphate (2.65 g), sodium acetate (4.0 g), industrial methylated spirit (56 ml) and water (23 ml) was stirred at ambient temperature for sixteen hours. The reaction mixture was extracted with ether. The ether extract was washed with water, dried and evaporated to give a solid which was recrystallised from petroleum ether (b.p. 80°–100° C.) to give 1-[1-(3,4-dichlorophenyl)cyclobutyl]butan-2-one oxime (m.p. 106°–110° C.).

A solution of trifluoroacetic acid (2.33 ml) in tetrahydrofuran (5 ml) was added to a stirred suspension of sodium borohydride (1.13 g) in tetrahydrofuran (30 ml) over a period of five minutes. A solution of the oxime (1.7 g) prepared as described above in tetrahydrofuran (25 ml) was added dropwise and the mixture heated under reflux for six hours. The mixture was cooled and water (25 ml) and then 5 N sodium hydroxide solution (25 ml) were added. The mixture was extracted with ether and the extract washed with water, dried and evaporated to give a residue which was dissolved in petroleum ether (25 ml). Dry hydrogen chloride gas was passed through the ether solution to give 1-{[1-(3,4-dichlorophenyl)cyclobutyl]methyl}propylamine hydrochloride (m.p. 222°–224° C.). (Formula I $R_1$, $R_2$, $R_3$ and $R_4$=H; $R_5$=4-Cl; $R_6$=3-Cl; $R_7$=Et and $R_8$=H).

EXAMPLE 18

A solution of 1-[1-(3,4-dichlorophenyl)cyclobutyl]-butan-2-one (5.0 g) prepared as described in Example 17 and methoxy-amine hydrochloride (1.63 g) in a mixture of pyridine (60 ml) and ethanol (60 ml) was heated under reflux for 72 hours. The reaction mixture was evaporated to dryness and a mixture of water and ether added to the residue. The ether layer was washed with sodium bicarbonate solution and water, dried and evaporated to give 1-[1-(3,4-dichlorophenyl)cyclobutyl]butan-2-one oxime O-methyl ether.

The oxime ether prepared as described above (15 g) was then reduced to the product of Example 17 using sodium borohydride (0.95 g) in a similar manner to that described in Example 17.

EXAMPLE 19

Sodium cyanoborohydride (0.4 g) was added to a solution of 1-[1-(3,4-dichlorophenyl)cyclobutyl]butan-2-one (2.45 g) prepared as described in Example 16 and ammonium acetate (7 g) in methanol (28 ml) and the mixture stirred at room temperature for four days. Water (25 ml) was added dropwise with cooling. The aqueous mixture was extracted with ether and the ether layer washed with water and 5 N hydrochloric acid (50 ml). The compound of Example 17 precipitated as a white solid.

EXAMPLE 20

2-[1-(4-Chlorophenyl)cyclobutyl]acetic acid (1.5 g prepared as described in Example 12) was heated under reflux with thionyl chloride. Excess thionyl chloride was removed in vacuo and the residue added dropwise to a solution of cyclopropylamine (0.94 g) in ether (10 ml) and the mixture stirred for thirty minutes. Water was added and the aqueous phase extracted with ether. The ether extract was dried and the ether removed to give 2-[1-(4-chlorophenyl)cyclobutyl]-N-cyclopropylacetamide.

A solution of the amide prepared as above (1.45 g) in ether (15 ml) was added dropwise to a stirred suspension of lithium aluminium hydride (0.42 g) in ether (7.5 ml) under nitrogen. The mixture was stirred at ambient temperature for one hour and then heated under reflux for a further two hours. After cooling, water (0.45 ml), then 15% sodium hydroxide solution (0.45 ml) and then water (1.35 ml) were added and the mixture stirred for fifteen minutes. The mixture was filtered and extracted with ether. The ether extract was shaken with N hydrochloric acid and a solid formed in the aqueous layer. The solid was N-cyclopropyl-2-[1-(4-chlorophenyl)cyclobutyl]ethylamine hydrochloride (m.p. 166°–170° C.).

A mixture of the hydrochloride salt (0.41 g) prepared as described above, sodium formate (0.1 g), 98% formic acid (1 ml) and 37–40% aqueous formaldehyde solution (0.5 ml) was heated at 85°–90° C. for eighteen hours. The reaction mixture was cooled and extracted with ether. The ether extract was washed with water, dried and filtered. Hydrogen chloride gas was passed through the filtrate which was then evaporated to leave a gum which was, warmed to give a solid which was N-cyclopropyl-N-methyl-2-[1-(4-chlorophenyl)cyclobutyl]ethylamine hydrochloride (m.p. 149°–153° C.). (Formula I $R_1$ and $R_2$=H; $R_3$=cyclopropyl; $R_4$=Me; $R_5$=4-Cl; $R_6$, $R_7$ and $R_8$=H).

EXAMPLE 21

Pharmaceutical compositions containing any one of the compounds of formula I disclosed in Examples 1 to 20 are prepared in the following manner.

EXAMPLE 21(a)

Tablets are prepared from the following ingredients:

|  | Parts by Weight |
| --- | --- |
| Active Ingredient | 50.0 |
| Lactose | 78.5 |
| Polyvinylpyrrolidone | 5.0 |
| Maize Starch | 15.0 |
| Magnesium Stearate | 1.5 |

The active ingredient, the lactose and some of the starch are mixed and granulated with a solution of the polyvinylpyrrolidone in ethanol. The granulate is mixed with the stearic acid and the rest of the starch and the mixture is compressed in a tabletting machine to give tablets containing 50.0 mg. of the active ingredient.

EXAMPLE 21(b)

Capsules are prepared in the following way. A mixture of the active ingredient (45 parts by weight) and lactose powder (205 parts by weight) is filled into hard gelatin capsules, each capsule containing 45 mg. of the active ingredient.

EXAMPLE 21(c)

In the preparation of enteric coated tablets, the tablets described in Example 21(b) are given a thin coat of shellac varnish, followed by 20 coats of cellulose acetate phthalate in a manner well known in the art. In a similar manner the capsules of Example 21(b) may be provided with an enteric coating.

EXAMPLE 21(d)

Vials containing a solution of water-soluble compounds of the present invention suitable for injection are prepared from the following ingredients:

| Active Ingredient | 1100 g. |
|---|---|
| Mannitol | 1100 g. |
| Water, freshly distilled | to 11 liters |

The active ingredient and mannitol are dissolved in some of the water and the volume of the solution is adjusted to 11 liters. The resulting solution is sterilised by filtration and filled into sterile vials each containing 1.65 ml. of solution.

EXAMPLE 21(e)

In the preparation of suppositories, 100 parts by weight of the finely ground active ingredient is incorporated in 1214 parts by weight of triglyceride suppository base and the mixture is formed into suppositories each containing 100 mg. of the active ingredient.

We claim:

1. A compound of the formula I

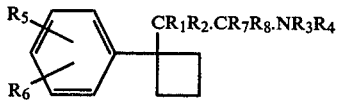

in which $R_1$ is H or an alkyl group containing 1 to 3 carbon atoms;

in which $R_2$ is H or an alkyl group containing 1 to 3 carbon atoms;

in which $R_3$ and $R_4$, which are the same or different, are selected from the group consisting of H, a straight or branched chain alkyl group containing 1 to 4 carbon atoms, and a cycloalkyl group in which the ring contains 3 to 7 carbon atoms, or $R_3$ and $R_4$ together with the nitrogen atom to which they are attached form a heterocyclic ring selected from the group consisting of pyrrolidinyl, piperidinyl and piperazinyl, each optionally substituted by one or more methyl groups, and 1, 2, 3, 6-tetrahydropyridyl;

in which $R_5$ and $R_6$ which are the same or different are selected from the group consisting of H, halo, an alkyl group containing 1 to 3 carbon atoms, and trifluoromethyl (with the proviso that one of $R_5$ and $R_6$ is halo), or $R_5$ and $R_6$, together with the carbon atoms to which they are attached, form a second benzene ring;

and in which $R_7$ and $R_8$ which are the same or different are H or an alkyl group containing 1 to 3 carbon atoms; and pharmaceutically-acceptable salts thereof.

2. A compound of the formula I as claimed in claim 1 in which $R_1$ is H or methyl and $R_2$ is H.

3. A compound of the formula I as claimed in claim 1 in which $R_3$ and $R_4$ are selected from the group consisting of H, methyl and ethyl.

4. A compound of the formula I as claimed in claim 1 in which $R_5$ and $R_6$ are selected from the group consisting of H, fluoro, chloro, bromo, iodo, trifluoromethyl, and methyl (with the proviso that one of $R_5$ and $R_6$ is chloro) or $R_5$ and $R_6$ together with the carbon atoms to which they are attached form a second benzene ring.

5. A compound of the formula I as claimed in claim 1 in which $R_7$ is H, methyl or ethyl and $R_8$ is H.

6. A compound of the formula II

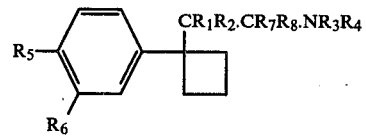

in which $R_1$ is H or an alkyl group containing 1 to 3 carbon atoms;

in which $R_2$ is H or an alkyl group containing 1 to 3 carbon atoms;

in which $R_3$ and $R_4$, which are the same or different, are selected from the group consisting of H, a straight or branched chain alkyl group containing 1 to 4 carbon atoms, and a cycloalkyl group in which the ring contains 3 to 7 carbon atoms, or $R_3$ and $R_4$ together with the nitrogen atom to which they are attached form a heterocyclic ring selected from the group consisting of pyrrolidinyl, piperidinyl and piperazinyl, each optionally substituted by one or more methyl groups, and 1, 2, 3, 6-tetrahydropyridyl;

in which $R_5$ and $R_6$ which are the same or different are selected from the group consisting of H, halo, an alkyl group containing 1 to 3 carbon atoms, and trifluoromethyl (with the proviso that one of $R_5$ and $R_6$ is halo), or $R_5$ and $R_6$, together with the carbon atoms to which they are attached, form a second benzene ring;

and in which $R_7$ and $R_8$ which are the same or different are H or an alkyl group containing 1 to 3 carbon atoms; and pharmaceutically-acceptable salts thereof.

7. A compound of the formula II as claimed in claim 6 in which $R_1$ is H or methyl and $R_2$ is H.

8. A compound of the formula II as claimed in claim 6 in which $R_3$ and $R_4$ are selected from the group consisting of H, methyl and ethyl.

9. A compound of the formula II as claimed in claim 6 in which $R_5$ and $R_6$ are selected from the group consisting of H, fluoro, chloro, bromo, iodo, trifluoromethyl, and methyl (with the proviso that one of $R_5$ and $R_6$ is chloro) or $R_5$ and $R_6$ together with the carbon atoms to which they are attached form a second benzene ring.

10. A compound of the formula II as claimed in claim 6 in which $R_7$ is H, methyl or ethyl and $R_8$ is H.

11. A compound of the formula III

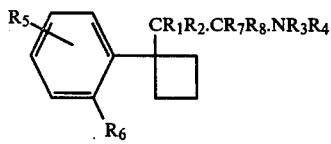

in which $R_1$ is H or an alkyl group containing 1 to 3 carbon atoms;

in which $R_2$ is H or an alkyl group containing 1 to 3 carbon atoms;

in which $R_3$ and $R_4$, which are the same or different, are selected from the group consisting of H, a straight or branched chain alkyl group containing 1 to 4 carbon atoms, and a cycloalkyl group in which the ring contains 3 to 7 carbon atoms, or $R_3$ and $R_4$ together with the nitrogen atom to which they are attached form a heterocyclic ring selected from the group consisting of pyrrolidinyl, piperidinyl and piperazinyl, each optionally substituted by one or more methyl groups, and 1, 2, 3, 6-tetrahydropyridyl;

in which $R_5$ is selected from the group consisting of halo, trifluoromethyl, and an alkyl group containing 1 to 3 carbon atoms;

in which $R_6$ is fluoro;

and in which $R_7$ and $R_8$ which are the same or different are H or an alkyl group containing 1 to 3 carbon atoms; and pharmaceutically-acceptable salts thereof.

12. A compound of the formula III as claimed in claim 11 in which $R_1$ is H or methyl and $R_2$ is H.

13. A compound of the formula III as claimed in claim 11 in which $R_3$ and $R_4$ are selected from the group consisting of H, methyl and ethyl.

14. A compound of the formula III as claimed in claim 11 in which $R_5$ is selected from the group consisting of fluoro, chloro, bromo, iodo, trifluoromethyl and methyl.

15. A compound of the formula III as claimed in claim 11 in which $R_7$ is H, methyl or ethyl and $R_8$ is H.

16. A compound of the formula II

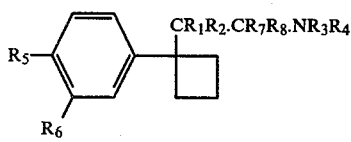

in which $R_1$ and $R_2$ are H, $R_3$ is H or methyl, $R_4$ is H or methyl or $R_3$ and $R_4$ together with the nitrogen atom to which they are attached form a pyrrolidine ring, $R_5$ is chloro or iodo, $R_6$ is H or chloro, $R_7$ is H, methyl or ethyl; $R_8$ is H and pharmaceutically-acceptable salts thereof.

17. Compound of claim 16 which is N,N-dimethyl-2-[1-(3,4-dichlorophenyl)cyclobutyl]ethylamine and its pharmaceutically acceptable salts.

18. Compound of claim 16 which is N-methyl-2-[1-(4-chlorophenyl)cyclobutyl]-1-methylethylamine and its pharmaceutically acceptable salts.

19. Compound of claim 16 which is N-{2-[1-(4-chlorophenyl)cyclobutyl]-1-methyl}ethylpyrrolidine and its pharmaceutically acceptable salts.

20. Compound of claim 16 which is 1-{[1-(3,4-dichlorophenyl)cyclobutyl]methyl}propylamine and its pharmaceutically acceptable salts.

21. Compound of claim 16 which is N,N-dimethyl-1-{[1-(3,4-dichlorophenyl)cyclobutyl]methyl}propylamine and its pharmaceutically acceptable salts.

22. Compound of claim 16 which is N,N-dimethyl-2-[1-(4-iodophenyl)cyclobutyl]ethylamine and its pharmaceutically acceptable salts.

23. A compound of the formula II

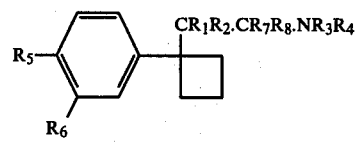

in which $R_1$ and $R_2$ are both H; $R_3$ is H or methyl; $R_4$ is H or methyl or $R_3$ and $R_4$ together with the nitrogen atom to which they are attached form a heterocyclic ring selected from the group consisting of pyrrolidinyl, piperidinyl and piperazinyl, each optionally substituted by one or more methyl groups, and 1,2,3,6-tetrahydropyridyl; $R_5$ is chloro or iodo; $R_6$ is H or chloro; $R_7$ is H, methyl or ethyl; and $R_8$ is H, and pharmaceutically-acceptable salts thereof.

24. A pharmaceutical composition suitable as an antidepressant comprising a therapeutically effective amount of a compound of formula I as claimed in claim 1 and a pharmaceutically-acceptable diluent or carrier.

25. A pharmaceutical composition suitable as an antidepressant comprising a therapeutically effective amount of a compound of formula II as claimed in claim 6 and a pharmaceutically-acceptable diluent or carrier.

26. A pharmaceutical composition suitable as an antidepressant comprising a therapeutically effective amount of a compound of formula III as claimed in claim 11 and a pharmaceutically-acceptable diluent or carrier.

27. A pharmaceutical composition as claimed in claim 24 in unit dosage form.

28. A pharmaceutical composition as claimed in claim 25 in unit dosage form.

29. A pharmaceutical composition as claimed in claim 26 in unit dosage form.

30. A method of treating depression which comprises administering to a patient a therapeutically effective amount of a compound of formula I as defined in claim 1.

31. A method of treating depression which comprises administering to a patient a therapeutically effective amount of a compound of formula II as defined in claim 6.

32. A method of treating depression which comprises administering to a patient a therapeutically effective amount of a compound of formula III as defined in claim 11.

* * * * *

UNITED STATES PATENT AND TRADEMARK OFFICE
CERTIFICATE OF CORRECTION

PATENT NO. : 4,443,449
DATED : April 17, 1984
INVENTOR(S) : James E. Jeffery and Eric C. Wilmshurst It is certified that error appears in the above—identified patent and that said Letters Patent is hereby corrected as shown below:

Title Page, [73] Assignee; "The Boots Company Limited" should read -- The Boots Company PLC --

Col. 2, line 50; insert a -- . -- after "fluoro"

Col. 6, line 68; change "." after the word "methyl" to -- ; --

Col. 7, line 7; change "." after the letter "H" to -- ; --

Col. 25, Claim 17, line 3; insert a dash -- - -- after the word "pharmaceutically"

Col. 26, Claims 18, 19, 20, 21 and 22, line 3; insert a dash, -- - -- after the word "pharmaceutically" in all instances

UNITED STATES PATENT AND TRADEMARK OFFICE
CERTIFICATE OF CORRECTION

PATENT NO. : 4,443,449

DATED : April 17, 1984

INVENTOR(S) : James E. Jeffery and Eric C. Wilmshurst

It is certified that error appears in the above—identified patent and that said Letters Patent is hereby corrected as shown below:

Col. 4, lines 25 & 36; change the "." to a -- , -- in both instances

Col. 5, line 4; "borohyride," should read -- borohydride, --

Col. 6, line 48; "alkylene" should read -- alkyl --

Col. 8, line 34; after "and" insert -- $R_3$ and --

Col. 12, line 12; "solid" should read -- sold --

Col. 16, line 26; "with" first occurrence should read -- was --

Col. 18, line 34; "piperididine" should read -- piperidine --

Col. 23, line 11; "(b)" should read -- (a) --

Col. 25, Claim 17, line 1; insert -- , -- after "16"

Col. 26, Claims 18, 19, 20, 21 and 22, line 1; insert -- , -- after "16" in all instances Signed and Sealed this Second Day of April 1985

[SEAL]

Attest:

DONALD J. QUIGG

*Attesting Officer*   *Acting Commissioner of Patents and Trademarks*